United States Patent [19]

Guillemin et al.

[11] 4,162,977
[45] Jul. 31, 1979

[54] MEANS FOR REMOVABLY SECURING SEPARATION COLUMN WITHIN COLUMN CHROMATOGRAPHY APPARATUS

[75] Inventors: Claude Guillemin, Paris; Christian Mayen, Creteil, both of France

[73] Assignee: Prolabo, Paris, France

[21] Appl. No.: 881,916

[22] Filed: Feb. 28, 1978

[30] Foreign Application Priority Data

May 2, 1977 [FR] France .................................. 77 14000

[51] Int. Cl.² ............................................. B01D 15/08
[52] U.S. Cl. .................................... 210/198 C; 55/386
[58] Field of Search ............... 210/198 C; 55/386, 197

[56] References Cited

U.S. PATENT DOCUMENTS

| 3,440,864 | 4/1969 | Blume | 210/198 C |
|---|---|---|---|
| 3,771,659 | 11/1973 | Fraser | 55/386 |
| 4,070,284 | 1/1978 | Fujita et al. | 210/198 C |
| 4,079,009 | 3/1978 | Seiler | 55/386 X |

Primary Examiner—John Adee
Attorney, Agent, or Firm—Burns, Doane, Swecker & Mathis

[57] ABSTRACT

A separation column is removably affixed within a column chromatography apparatus by means of a column engaging member, e.g., a concentric tube, and by securing a dispensing head of the apparatus to such member and engaged column via substantially axial compressive strength applied through said column engaging member.

8 Claims, 2 Drawing Figures

U.S. Patent     Jul. 31, 1979     4,162,977
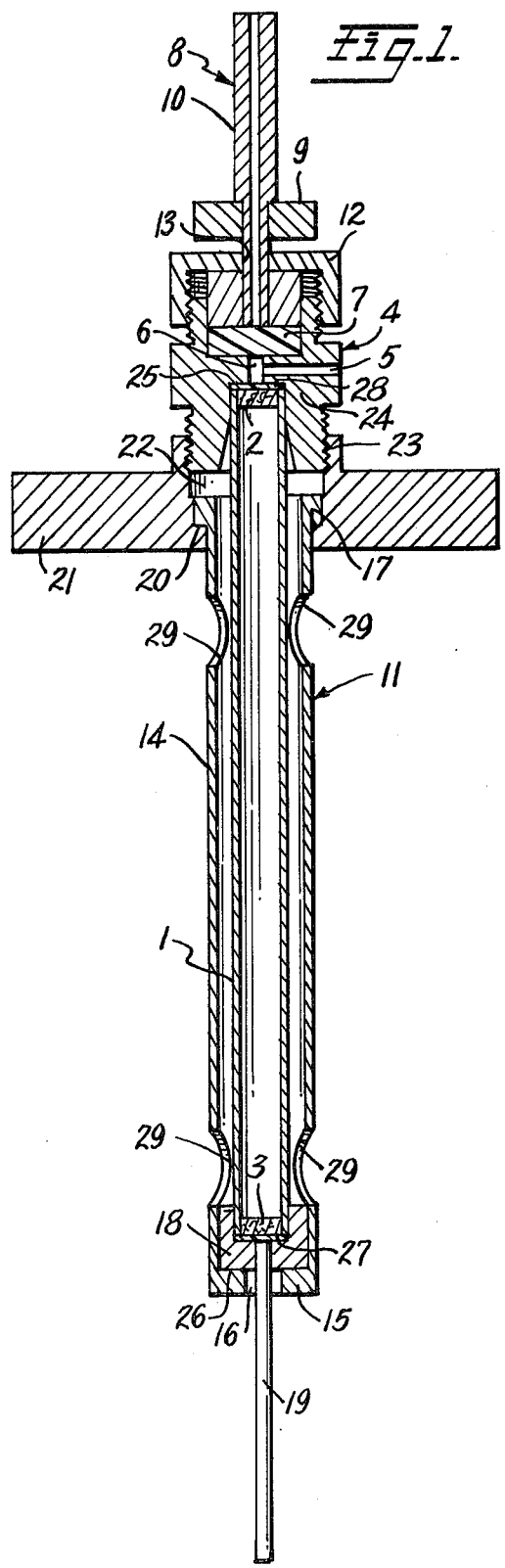
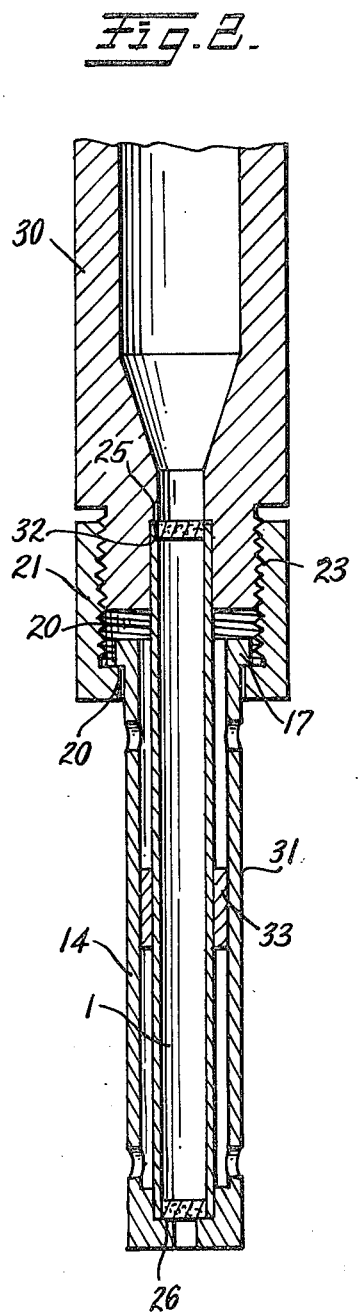

MEANS FOR REMOVABLY SECURING SEPARATION COLUMN WITHIN COLUMN CHROMATOGRAPHY APPARATUS

BACKGROUND OF THE INVENTION

1. Field of the Invention

The present invention relates to means for engaging and securing the column of chromatography apparatus to a given support and, more especially, to securing the column to its injection head or moving phase/sample inlet cap, or to the inlet for filling the column itself.

The column chromatography apparatus may be a gas or a liquid/column chromatography apparatus.

2. Description of the Prior Art

A column chromatography apparatus of known type typically successively comprises, in the direction of flow:

(i) a carrier reservoir;

(ii) a carrier system, which conveys said carrier to the separation column;

(iii) a head for injecting the carrier into the separation column;

(iv) means for injecting the sample to be analysed;

(v) a separation column wherein the analysis or preparative separation takes place, e.g., where the sample is separated into its various constituents, said column being filled with a continuous or stationary phase, e.g., a particulate adsorbent, packing or substrate; and (vi) a detector, selected depending upon the nature of the molecules to be developed.

The performance of a chromatography column is affected by the geometry of the various components of the injection head/column assembly, in particular by the presence of dead space, and also by the precision of the injection of the sample to be analyzed into the top of the column.

In the usual instrument, the sample injection system (whether it be of syringe-and-membrane type, or operating by means of a valve with a sampling loop) and the column for separation are separate and distinct entities, being connected to each other by means of any suitable coupling invariably comprising a significant dead volume. Such a coupling is usually by clamping by means of a sleeve or of a sleeve and collar acting in concert, not uncommonly resulting in crimping of the sleeve or, more often, causing permanent deformations in the walls of the separation column. These deformations make it difficult or even impossible to ultimately fixedly mount the separation column to another member, instrument, or support. In addition to this lack of operational flexibility, such approach mandates that same or all of the couplings be replaced with each new installation; often, complete replacement of the separation column is required.

Similar couplings are also used to secure the separation column to its feed inlet, namely, to the means for filling the column with the continuous or stationary phase, commonly a particulate, differential adsorbent.

SUMMARY OF THE INVENTION

Accordingly, a primary object of this invention is to provide means for enabling the ready engaging and securing of a chromatographic separation column to a support, which permits separation columns to be markedly interchangeable and easily and quickly mounted and removed without tools.

Another object of the invention is to eliminate the need for any couplings whatsoever and, thus, reduce the drawbacks resulting from their use.

Briefly, there has now been discovered a device which permits biasing a chromatographic separation column against the bearing surface of a support and securing it to said support, said support being, more specifically, a device for filling said column with its stationary phase or the injection head of a chromatography apparatus, and characterized by the fact that it comprises means to subject said column to a substantially axial compressive stress.

In the device according to this invention, one end of the separation column is firmly biased against the bearing surface of its support, which is desirably either a filling device therefor or the injection head of a chromatography apparatus, by a substantially axial compressive stress applied at the other end of the column. The device according to the invention comprises simple means for establishing and maintaining such stress. Such stress is established and maintained via bearing area and cooperating bearing surface for either end of the column, the bearing area and the bearing surface being of course connected to each other and interdependent. The connection between the bearing area and the bearing surface of the support comprises means for adjusting the distance between the bearing area and the bearing surface of the support, in order to conveniently compensate for differences in the actual lengths of columns having the same general length.

BRIEF DESCRIPTION OF THE DRAWINGS

In the drawings:

FIG. 1 is a cross-sectional view through an axial plane of symmetry of one embodiment of the device according to this invention, depicting a separation column engaged and secured to the injection head of a chromatography apparatus; and FIG. 2 is a cross-sectional view through an axial plane of symmetry of another embodiment of the device according to the invention, depicting the separation column engaged and secured to a filling means therefor.

DETAILED DESCRIPTION OF THE INVENTION

Referring specifically to the figures of drawing, the device according to the embodiment illustrated in FIG. 1 permits engaging and securing a separation column 1 to the injection head of a chromatography apparatus. The column 1, filled with suitable continuous or stationary phase and fitted with two end discs 2, 3 of fritted material, is ready for use. It is securedly engaged to the injection head 4 by means of the device 11 which is one object of the invention.

The injection head 4 is provided with a conduit 5 for introducing the carrier and a conduit 6 for injecting the sample to be analyzed. The carrier feed line from the reservoir (not shown) is connected by the commonly employed means, such as, for example, a coupling screwed onto the conduit 5 of the injection head 4.

The injection of the sample has been depicted on FIG. 1 as taking place through a syringe passing through a thin partition or membrane 7 consisting, for example, of an elastomer. The membrane 7 may be held in place by a cap 12 which may be screwed on, for example, and which is centrally apertured with a hole 13. In order to ensure good analytical reproducibility, the preferred approach is for the injection head 4 to be provided with a device 8 for guiding the syringe needle, containing a stop block 9 and a centering guide 10 for the needle (not shown). The needle centering guide 10 extends through the hole 13 in the cap 12 which holds the membrane 7 in place. The stop block 9 permits placement of the end of the syringe needle to the same depth within the separation column when injecting samples, and upon repeated use. Instead of being injected with a syringe, the sample may equally as well be injected by means of a sampling valve.

The conduit 5 used to introduce the carrier and the conduit 6 used to inject the sample converge to establish concurrent flow and ultimately define a zone of axial enlargement or compartment 24, generally cylindrical in shape, provided with a bearing surface 25, typically a flat surface, as illustrated. One end of the separation column 1 is fitted within said compartment 24.

The device 11 according to this invention comprises a substantially cylindrical, concentric column engaging tube 14, closed at one end by a wall member 15 provided with a hole 16 and provided at its other end with an external annular flange 17. The wall 15 constitutes the bearing area 26 for the end of the separation column. The column-engaging tube 14 connects said bearing area 26 to the support, namely, the injection head 4 in this embodiment.

A ferrule 18 is preferably provided between the end of the separation column 1 and the bearing area 26 to hold the effluent tube 19 leading to the detector (not shown).

The annular flange 17 butts against the shoulder 20 of the hollow center portion 22 of a disc-shaped nut 21 in order to facilitate manual operation. The nut 21 is provided with a thread 23 in the region opposite the shoulder of the hollow center 22. This thread 23 engages a correspondingly threaded area of the injection head 4.

The separation column 1 is biased against the bearing surface 25 of the injection head 4 by the substantially axial compressive stress applied to the end of the separation column 1 via the wall 15 of the tube 14, through the bearing area 26 and the ferrule 18. This compressive stress is generated by biasing together the bearing area 26 and the bearing surface 25 by means of the nut 21 and the thread 23 which permit adjusting the distance between the bearing area 26 and the bearing surface 25 borne by the support.

Preferably, and in order to improve the tightness of the seals between the injection head 4 and the separation column 1 and between the separation column 1 and the ferrule 18, gaskets or seals 27, 28 are installed within the compartment 24 of the injection head 4 and within the ferrule 18 before mounting the separation column 1 in place. Said seals may be toroidal or flat; polytetrafluoroethylene seals are particularly suitable. The seals 27, 28 are advantageously inlaid within grooves provided in the bearing area 26 and bearing surface 25.

The column engaging tube 14 contains windows, such as 29, in its walls to allow checking the proper positioning of the column and the absence of leaks at the joints, in the event of improper sealing. The column engaging tube 14 can also be provided with lateral tubes to permit establishing, for example, a flow of isothermal fluid in the annular space between the separation column 1 and the column-engaging tube 14 in order to perform analyses at constant temperature.

The device according to the invention, in the embodiment illustrated in FIG. 2, enables engaging and securing of a chromatographic separation column to a filling device.

Liquid-phase chromatography separation columns typically are filled with a porous chromatographic substrate as particulate adsorbent selected depending upon the various constituents of the sample to be analyzed. The substrate should be very compact and very homogeneous, so that there are no paths of preferential flow. Such is obtained by filling the empty separation column with a thick paste composed of the chromatograhic substrate in suspension in a solvent, using a high-pressure pump, generally operating at a pressure of about 400 bars. The chromatographic substrate is retained by the disc of fritted material mounted at the downside end of the separation column and is compacted by pressure.

The device according to the invention depicted in FIG. 2 is similar to the device depicted in FIG. 1 which permits engaging and securing the separation column to an injection head for the chromatography apparatus, which latter device has been above described.

In the device 31 depicted in FIG. 2, the separation column 1 is attached to a support which is in this embodiment a pressure-resistant reservoir 30 having an inverted conical or tapered outlet; this reservoir being designed to hold the substrate paste. A coupling in the upper region of said reservoir (not shown) permits filling and connection with the high-pressure pump; alternately, said reservoir may be connected to a reserve of substrate paste by any suitable valve means. The outlet end of the reservoir 30 defines a compartment which is generally cylindrical in shape and is provided with a generally flat bearing surface 25 for the inlet end of the separation column.

Similar to the tube 11 depicted in FIG. 1, the device 31 depicted here comprises a bearing area 26 for the outlet end of the separation column 1, which is effectively interconnected with the support, namely, to the reservoir 30, by the column-holder of column-engaging tube 14. The other end of the column-engaging tube 14 bears an annular flange 17 which butts against the shoulder 20 of the hollow center 22 of the nut 21. The hollow center 22 of the nut 21 is threaded and engages the corresponding, similarly threaded portion of the conical reservoir 30.

The separation column 1 is biased against the bearing surface 32 of the reservoir 30 by the substantially axial compressive stress applied via the bearing area 26 of the column-engaging tube 14. Said compressive stress is generated by bringing together the bearing area 26 and the bearing surface 25 by simple turning of the nut 21 along the threading 23.

In order to improve the tightness of the seal between the separation column 1 and the reservoir 20, a gasket or seal 32 may be provided against the bearing surface 25 before mounting the separation column in place.

The column-engaging tube 14 may contain a zone provided with strengthening or reinforcing means which may consist, for example, of one or more internal shoulders 33, in order to prevent the separation column from buckling as the nut 21 is screwed on the reservoir 30; the separation column thus being maintained in the proper position.

The devices according to the invention described above include a column-engaging tube 14 whose length is selected according to the length of the separations columns used. Thus, column-engaging tubes of various lengths or of adjustable length (such as column-engaging tubes consisting of several sections mounted telescopically and locked to each other) may be used. Column-engaging tubes are generally used whose length permits using separation columns ranging from 0.5 to 100 centimeters in length, preferably from 1 to 50 centimeters in length.

The inside diameter of the column-engaging tube is determined by the outside diameter of the separation column. Nevertheless, separation columns having different outside diameters can be used with the same column-engaging tube, provided it is of course possible to insert said separation columns into the columns into the column-engaging tube.

Thus, column-engaging tubes can be utilized with an inside diameter but slightly larger than the outside diameter of the separation column, which columns will thus be held firmly throughout their length and will be prevented from buckling as the nut is tightened.

Clearly, the invention is not limited to the embodiments specifically described above, and many variations are possible without going beyond the scope of this invention. Such variations include, but are not limited to:

For example, the adjustable means consisting of the nut together with the screw thread borne by the support may be replaced by, for example, hydraulic or pneumatic jacks, or by a system of flanges joined by bolts, or even by a cam or lever system.

One end of the column-engaging tube may also be directly attached to the support by, for example, a bayonet lock, namely, by a system which does not include any means of adjusting the distance between the bearing area and the support; either the inside surface or the outside surface of the other end of the column-engaging tube will then have a thread onto which is screwed a nut integral with the bearing surface.

The device which is the object of the invention, which permits ready engaging and securing of a chromatographic separation column to a support, said support advantageously being a device for filling the column or the injection head of a chromatography apparatus, exhibits numerous advantages.

An important advantage of the device is that it permits quick and effective interchangeability of separation columns; it also permits quick, easy mounting and removal without the need for any tools.

Furthermore, the separation columns are not subjected to any deformation, since the device does not require the use of the couplings that normally deform a column; the separation columns are thus reusable and, moreover, are less complex and less costly.

Even after the columns have been mounted and removed several times, the same retain a satisfactory seal which can readily be verified by use of pressures of over 100 bars.

Moreover, as the separation column is mounted on the injection head of a chromatography apparatus, dead volumes are practically non-existent, resulting in an especially marked improvement in analytical effectiveness.

The device also enables convenient access for the filling of the separation columns, resulting in maximum effectiveness for the substrate.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In chromatography apparatus including a dispensing head, a device for removably securing chromatography separation column means in operative relationship to said dispensing head, said device including:
    a generally tubular engagement column adapted to receive and carry said separation column means, and including means at one end thereof defining a first bearing surface arranged to be engageable with one axial end of separation column means carried thereby;
    means for removably connecting the other end of said engagement column with said dispensing head, said dispensing head having a second bearing surface thereon arranged to confront the other axial end of separation column means carried by said engagement column when said engagement column is connected with said dispensing head; and
    adjustable means for applying a selected, substantially axial compressive stress to separation column means carried by said engagement column when the other end of said engagement column is connected with said dispensing head, said stress being applied through said engagement column and said first and said second bearing surfaces, whereby to secure said separation column means carried by said engagement column in operative relationship with said dispensing head.

2. In chromatography apparatus as recited in claim 1, wherein said connecting means comprises interengageable thread means carried by said other end of said engagement column and by said dispensing head.

3. In chromatography apparatus as recited in claim 2, wherein said adjustable means for applying a selected substantial axial compressive stress to separation column means carried by said engagement column comprises thread means engageable with said engagement column.

4. In chromatography apparatus as recited in claim 3, wherein said thread means for applying a selected substantial axial compressive stress is combined with said thread means for connecting said engagement column with said dispensing head.

5. In chromatography apparatus as recited in claim 1, wherein said first bearing surface is formed by an integral end wall of said engagement column.

6. In chromatography apparatus as recited in claim 1, wherein said generally tubular engagement columm has an internal diameter only slightly larger than separation column means to be received therein.

7. In chromatography apparatus as recited in claim 1, further including:
    seal means located between said second bearing surface and the other axial end of separation column means received in said engagement column.

8. In chromatography apparatus as recited in claim 1, wherein said engagement column is provided with viewing openings therein, for viewing separation column means received therein.

* * * * *